United States Patent
Blank et al.

(10) Patent No.: US 7,206,623 B2
(45) Date of Patent: Apr. 17, 2007

(54) OPTICAL SAMPLING INTERFACE SYSTEM FOR IN VIVO MEASUREMENT OF TISSUE

(75) Inventors: Thomas B. Blank, Chandler, AZ (US); George Acosta, Phoenix, AZ (US); Mutua Mattu, Gilbert, AZ (US); Marcy Makarewicz, Chandler, AZ (US); Stephen L. Monfre, Gilbert, AZ (US); Alexander D. Lorenz, Phoenix, AZ (US); Timothy L. Ruchti, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 323 days.

(21) Appl. No.: 10/170,921

(22) Filed: Jun. 12, 2002

(65) Prior Publication Data

US 2003/0069484 A1 Apr. 10, 2003

Related U.S. Application Data

(63) Continuation-in-part of application No. 09/563,782, filed on May 2, 2000, now Pat. No. 6,415,167.

(51) Int. Cl.
*A61B 5/00* (2006.01)
(52) U.S. Cl. ...................... 600/344; 600/310
(58) Field of Classification Search ........ 600/309–310, 600/322–323, 344
See application file for complete search history.

(56) References Cited

U.S. PATENT DOCUMENTS

| 4,033,054 | A | * | 7/1977 | Fukuoka ..................... 606/204 |
| 4,321,930 | A | * | 3/1982 | Jobsis et al. ................ 600/344 |
| 5,170,786 | A | * | 12/1992 | Thomas et al. ............. 600/310 |
| 5,285,783 | A | | 2/1994 | Secker |
| 5,299,570 | A | * | 4/1994 | Hatschek ..................... 600/479 |
| 5,448,662 | A | | 9/1995 | Kittel et al. |
| 5,492,118 | A | | 2/1996 | Gratton et al. |

(Continued)

FOREIGN PATENT DOCUMENTS

DE 26 40 987 3/1978

(Continued)

OTHER PUBLICATIONS

Webster's II New Riverside University Dictionary, Riverside Publishing Company, 1994, p. 1000.*

*Primary Examiner*—Eric F. Winakur
(74) *Attorney, Agent, or Firm*—Michael A. Glenn; Glenn Patent Group

(57) ABSTRACT

An optical sampling interface system minimizes and compensates error resulting from sampling variations and measurement site state fluctuations. Components include: An optical probe placement guide having an aperture wherein the optical probe is received, facilitates repeatable placement accuracy on surface of a tissue measurement site with minimal, repeatable disturbance to surface tissue. The aperture creates a tissue meniscus that minimizes interference due to surface irregularities and controls variation in tissue volume sampled; an occlusive element placed over the tissue meniscus isolates the meniscus from environmental fluctuations, stabilizing hydration at the site and thus, surface tension; an optical coupling medium eliminates air gaps between skin surface and optical probe; a bias correction element applies a bias correction to spectral measurements, and associated analyte measurements. When the guide is replaced, a new bias correction is determined for measurements done with the new placement. Separate components of system can be individually deployed.

24 Claims, 5 Drawing Sheets

U.S. PATENT DOCUMENTS

| | | | |
|---|---|---|---|
| 5,506,482 | A * | 4/1996 | Teramatsu et al. .......... 315/382 |
| 5,548,674 | A | 8/1996 | Rondeau |
| 5,619,195 | A * | 4/1997 | Allen et al. ................... 341/20 |
| 5,636,634 | A | 6/1997 | Kordis et al. |
| 5,655,530 | A | 8/1997 | Messerschmidt |
| 5,661,843 | A | 8/1997 | Rickernbach et al. |
| 5,725,480 | A | 3/1998 | Oosta et al. |
| 5,769,076 | A * | 6/1998 | Maekawa et al. ........... 600/322 |
| 5,823,951 | A | 10/1998 | Messerschmidt |
| 5,825,488 | A | 10/1998 | Kohl et al. |
| 5,869,075 | A * | 2/1999 | Krzysik ...................... 424/414 |
| 5,879,373 | A * | 3/1999 | Roper et al. ................ 600/344 |
| 5,891,021 | A * | 4/1999 | Dillon et al. ............... 600/310 |
| 5,956,150 | A | 9/1999 | Kanne |
| 6,157,041 | A | 12/2000 | Thomas et al. |
| 6,240,306 | B1 | 5/2001 | Rohrscheib et al. |
| 6,381,489 | B1 * | 4/2002 | Ashibe ....................... 600/344 |
| 6,415,167 | B1 | 7/2002 | Blank |
| 6,421,549 | B1 * | 7/2002 | Jacques ...................... 600/331 |
| 6,441,388 | B1 | 8/2002 | Thomas et al. |
| 6,528,809 | B1 | 3/2003 | Thomas et al. |
| 6,585,370 | B2 * | 7/2003 | Zelman ...................... 351/103 |
| 6,788,965 | B2 | 9/2004 | Ruchti et al. |
| 2003/0040663 | A1 * | 2/2003 | Rule et al. .................. 600/309 |
| 2003/0216627 | A1 | 11/2003 | Lorenz et al. |
| 2004/0068163 | A1 | 4/2004 | Ruchti et al. |
| 2004/0127777 | A1 | 7/2004 | Ruchti et al. |

FOREIGN PATENT DOCUMENTS

| | | |
|---|---|---|
| JP | 1992-215742 | 10/2002 |
| WO | WO 96/28084 A1 | 9/1996 |
| WO | WO 97-05819 A | 2/1997 |
| WO | WO 00/22982 A | 4/2000 |
| WO | WO 00/42907 A1 | 7/2000 |
| WO | WO 00/76575 * | 12/2000 |

* cited by examiner

OPTICAL SAMPLING INTERFACE SYSTEM FOR IN VIVO MEASUREMENT OF TISSUE

CROSS REFERENCE TO RELATED APPLICATION

This application is a Continuation-in-part of U.S. patent application Ser. No. 09/563,782, filed on May 2, 2000, now U.S. Pat. No. 6,415,167, hereby incorporated in its entirety by reference.

BACKGROUND OF THE INVENTION

1. Field of the Invention

The invention relates to optical sampling of tissue in vivo. More particularly, the invention relates to an optical sampling interface system that includes an optical probe placement guide, a means for stabilizing the sampled tissue, an optical coupler for repeatably sampling a tissue measurement site in vivo, and a means for compensating measurement bias.

2. Technical Background

In vivo measurement of tissue properties and analytes using optically based analyzers requires that tissue measurement region be positioned and coupled with respect to an optical interface or probe. The requirements of an optical sampling interface system for such placement and coupling would depend upon the nature of the tissue properties and analytes under consideration, the optical technology being applied and the variability of the tissue with respect to the target analyte. Often, when sampling reproducibility is vital, the optical measurement is performed in a laboratory where the majority of the factors pertaining to the measurement can be controlled or constrained. However, there are many demanding in vivo applications that cannot be performed in a laboratory setting but yet require a high degree of optical sample reproducibility. Often, a relatively unskilled operator or user must perform the optical measurement. One such application is the non-invasive measurement of glucose through near-infrared spectroscopy. With the desired end result being an optical measurement system that can be used by the consumer in a variety of environments, the optical sampling requirements are stringent. This problem is further considered through a discussion of the target application, the structure of live skin and the dynamic properties of live tissue.

Noninvasive Measurement of Glucose

Diabetes is a leading cause of death and disability worldwide and afflicts an estimated 16 million Americans. Complications of diabetes include heart and kidney disease, blindness, nerve damage, and high blood pressure with the estimated total cost to United States economy alone exceeding $90 billion per year. See *Diabetes Statistics*. Publication No. 98-3926, National Institutes of Health, Bethesda MD (November 1997). Long-term clinical studies show that the onset of complications can be significantly reduced through proper control of blood glucose levels. See The Diabetes Control and Complications Trial Research Group, *The effect of intensive treatment of diabetes on the development and progression of long-term complications in insulin-dependent diabetes mellitus, N Eng J of Med,* 329:977–86 (1993). A vital element of diabetes management is the self-monitoring of blood glucose levels by diabetics in the home environment. A significant disadvantage of current monitoring techniques is that they discourage regular use due to the inconvenience and pain involved in drawing blood through the skin prior to analysis. Therefore, new methods for self-monitoring of blood glucose levels are required to improve the prospects for more rigorous control of blood glucose in diabetic patients.

Numerous approaches have been explored for measuring blood glucose levels, ranging from invasive methods such as microdialysis to noninvasive technologies that rely on spectroscopy. Each method has associated advantages and disadvantages, but only a few have received approval from certifying agencies. To date, no noninvasive techniques for the self-monitoring of blood glucose have been certified.

One method, near-infrared spectroscopy involves the illumination of a spot on the body with near-infrared electromagnetic radiation (light in the wavelength range 700–2500 nm). The light is partially absorbed and scattered, according to its interaction with the tissue constituents prior to being reflected back to a detector. The detected light contains quantitative information that is based on the known interaction of the incident light with components of the body tissue including water, fat, protein, and glucose.

Previously reported methods for the noninvasive measurement of glucose through near-infrared spectroscopy rely on the detection of the magnitude of light attenuation caused by the absorption signature of blood glucose as represented in the targeted tissue volume. The targeted tissue volume is that portion of irradiated tissue from which light is reflected or transmitted to the spectrometer detection system. The signal due to the absorption of glucose is extracted from the spectral measurement through various methods of signal processing and one or more mathematical models. The models are developed through the process of calibration on the basis of an exemplary set of spectral measurements and associated reference blood glucose values (the calibration set) based on an analysis of capillary (fingertip) or venous blood.

Near-infrared spectroscopy has been demonstrated in specific studies to represent a possible approach for the noninvasive measurement of blood glucose levels. M. Robinson, R. Eaton, D. Haaland, G. Keep, E. Thomas, B. Stalled, P. Robinson, *Noninvasive glucose monitoring in diabetic patients: A preliminary evaluation*, Clin Chem, 38:1618–22 (1992) reports three different instrument configurations for measuring diffuse transmittance through the finger in the 600–1300 nm range. Meal tolerance tests were used to perturb the glucose levels of three subjects and calibration models were constructed specific to each subject on single days and tested through cross-validation. Absolute average prediction errors ranged from 19.8 to 37.8 mg/dL. H. Heise, R. Marbach, T. Koschinsky, F. Gries, *Noninvasive blood glucose sensors based on near-infrared spectroscopy,* Artif Org, 18:439–47 (1994); H. Heise, R. Marbach, *Effect of data pretreatment on the noninvasive blood glucose measurement by diffuse reflectance near-IR spectroscopy*, SPIE Proc, 2089:114–5 (1994); R. Marbach, T. Koschinsky, F. Gries, H. Heise, *Noninvasive glucose assay by near-infrared diffuse reflectance spectroscopy of the human inner lip*, Appl Spectrosc, 47:875–81 (1993) and R. Marbach, H. Heise, *Optical diffuse reflectance accessory for measurements of skin tissue by near-infrared spectroscopy*, Applied Optics 34(4):610–21 (1995) present results through a diffuse reflectance measurement of the oral mucosa in the 1111–1835 nm range with an optimized diffuse reflectance accessory. In vivo experiments were conducted on single diabetics using glucose tolerance tests and on a population of 133 different subjects. The best standard error of prediction reported was 43 mg/dL and was obtained from a two-day single person oral glucose tolerance test that was evaluated through cross-validation.

K. Jagemann, C. Fischbacker, K. Danzer, U. Muller, B. Mertes, *Application of near-infrared spectroscopy for non-invasive determination of blood/tissue glucose using neural network*, Z Phys Chem, 191S: 179–190 (1995); C. Fischbacker, K. Jagemann, K. Danzer, U. Muller, L. Papenkrodt, J. Schuler, *Enhancing calibration models for noninvasive near-infrared spectroscopic blood glucose determinations*, Fresenius J Anal Chem 359:78–82 (1997); K. Danzer, C. Fischbacker, K. Jagemann, K. Reichelt, *Near-infrared diffuse reflection spectroscopy for noninvasive blood-glucose monitoring*, LEOS Newsletter 12(2):9–11 (1998); and U. Muller, B. Mertes, C. Fischbacker, K. Jagemann, K. Danzer, *Noninvasive blood glucose monitoring by means of new infrared spectroscopic methods for improving the reliability of the calibration models*, Int J Artif Organs, 20:285–290 (1997) recorded spectra in diffuse reflectance over the 800–1350 nm range on the middle finger of the right hand with a fiber-optic probe. Each experiment involved a diabetic subject and was conducted over a single day with perturbation of blood glucose levels through carbohydrate loading. Results, using both partial least squares regression and radial basis function neural networks were evaluated on single subjects over single days through cross-validation. Danzer, et al., supra, report an average root mean square measurement error of 36 mg/dL through cross-validation over 31 glucose profiles.

J. Burmeister, M. Arnold, G. Small, *Human noninvasive measurement of glucose using near infrared spectroscopy* [abstract], Pittcon, New Orleans La. (1998) collected absorbance spectra through a transmission measurement of the tongue in the 1429–2000 nm range. A study of five diabetic subjects was conducted over a 39-day period with five samples taken per day. Every fifth sample was used for an independent test set and the standard error of prediction for all subjects was greater than 54 mg/dL.

In T. Blank, T. Ruchti, S. Malin, S. Monfre, *The use of near-infrared diffuse reflectance for the noninvasive prediction of blood glucose*, IEEE Lasers and Electro-Optics Society Newsletter, 13:5 (October 1999), the reported studies demonstrate noninvasive measurement of blood glucose during modified oral glucose tolerance tests over a short time period. The calibration was customized for the individual and tested over a relatively short time period.

In all of these studies, diverse limitations were cited that would affect the acceptance of such a method as a commercial product. Fundamental to all the studies is the problem of the small signal attributable to glucose, particularly in view of the difficulty in obtaining a reproducible sample of a given tissue volume, as a result of the complex and dynamic nature of the tissue. For example, see O. Khalil, *Spectroscopic and clinical aspects of noninvasive glucose measurements*, Clin Chem, v. 45, pp. 165–77 (1999). The sampling problem is further accentuated by noting that the reported studies were performed under highly controlled conditions using skilled techniques rather than in a home environment by the consumer. As reported by S. Malin, T. Ruchti, *An Intelligent System for Noninvasive Blood Analyte Prediction*, U.S. Pat. No. 6,280,381 (Aug. 28, 2001), the entirety of which is hereby incorporated by reference, chemical, structural and physiological variations occur that produce dramatic and nonlinear changes in the optical properties of the tissue sample. See R. Anderson, J. Parrish, *The optics of human skin*, Journal of Investigative Dermatology, 7:1, pp. 13–19 (1981); W. Cheong, S. Prahl, A. Welch, *A review of the optical properties of biological tissues*, IEEE Journal of Quantum Electronics, 26:12, pp. 2166–2185, (December 1990); D. Benaron, D. Ho, *Imaging (NIRI) and quantitation (NIRS) in tissue using time-resolved spectrophotometry: the impact of statically and dynamically variable optical path lengths*, SPIE, 1888, pp. 10–21 (1993); J. Conway, K. Norris, C. Bodwell, *A new approach for the estimation of body composition: infrared interactance*, The American Journal of Clinical Nutrition, 40, pp. 1123–1140 (December 1984); S. Homma, T. Fukunaga, A Kagaya, *Influence of adipose tissue thickness in near infrared spectroscopic signals in the measurement of human muscle*, Journal of Biomedical Optics, 1:4, pp. 418–424 (October 1996); A. Profio, *Light transport in tissue*, Applied Optics, 28:12), pp. 2216–2222, (June 1989), M. Van Gemert, S. Jacques, H. Sterenborg, W. Star, *Skin optics*, IEEE Transactions on Biomedical Engineering, 36:12, pp. 1146–1154 (December 1989); and B. Wilson, S. Jacques, *Optical reflectance and transmittance of tissues: principles and applications*, IEEE Journal of Quantum Electronics, 26:12, pp. 2186–2199.

The measurement is further complicated by the heterogeneity of the sample, the multi-layered structure of the skin and the rapid variation related to hydration levels, changes in the volume fraction of blood in the tissue, hormonal stimulation, temperature fluctuations and blood analyte levels. This can be further considered through a discussion of the scattering properties of skin and the dynamic nature of the tissue.

Structure of Human Skin

The structure and pigmentation of human skin vary widely among individuals as well as between different sites on the same individual. Skin consists of a stratified, cellular epidermis, and an underlying dermis of connective tissue. Below the dermis is the subcutaneous fatty layer or adipose tissue. The epidermis is the thin outer layer that provides a barrier to infection and loss of moisture, while the dermis is the thick inner layer that provides mechanical strength and elasticity. The epidermis layer is 10–150 µm thick and can be divided into three layers, the basal, middle, and superficial layers. The basal layer borders the dermis and contains pigment-forming melanocyte cells, keratinocyte cells, Langherhan cells and Merkel cells See F. Ebling, *The normal skin*, In: *Textbook of Dermatology*, A. Rook, D. Wilkinson, F. Ebling, eds., 3ed., pp. 5–30, Blackwell Scientific Publishers, Oxford, England (1979). The superficial layer is also known as the stratum corneum (SC).

The stratum corneum, the outermost layer of the mammalian epidermis, is formed and continuously replenished by the slow upward migration of aqueous keratinocyte cells from the germinative basal layer of the epidermis. It is replenished about every 2 weeks in mature adults. See W. Montagna, *The Structure and Function of Skin,* 2ed., p. 454, Academic Press, New York, (1961). This complex process involving intracellular dehydration and synthesis of an insoluble protein, keratin, results in keratin-filled, biologically inactive, shrunken cells. These flat, dehydrated, hexagonal cells are tightly bound to their neighbors and each is approximately 30 µm wide and 0.8 µm deep. See H. Baker, *The skin as a barrier*, In: *Textbook of Dermatology*, A. Rook, D. Wilkinson, F. Ebling, eds., 3ed., pp. 5–30, Blackwell Scientific Publishers, Oxford, England (1979). There are about twelve to twenty cell layers over most of the body surface. The stratum corneum is typically 10–20 µm thick, except on the planar surfaces, where it is considerably thicker. See A. Kligman, *The Biology of the stratum corneum*, in: *The Epidermis*, W. Montagna, W. Lobitz, eds. Academic Press, New York, pp. 387–433 (1964).

The major constituent of the dermis, apart from water, is a fibrous protein, collagen, which is embedded in a ground substance composed mainly of protein and glycosaminoglycans. The glycosaminoglycans play a key role in regulating the assembly of collagen fibrils and tissue permeability to water and other molecules. See K. Trier, S. Olsen, T. Ammitzboll, *Acta. Ophthalmol.*, v. 69, pp. 304–306 (1990). Collagen is the most abundant protein in the human body. Elastin fibers are also plentiful though they constitute a smaller proportion of the bulk. The dermis also contains other cellular constituents and has a very rich blood supply, though no vessels pass the dermo-epidermal junction. See Ebling, supra. The blood vessels nourish the skin and control body temperature. In humans, the thickness of the dermis ranges from 0.5 mm over the eyelid to 4 mm on the back and averages approximately 1.2 mm over most of the body. See S. Wilson, V. Spence, *Phys. Med. Biol.* v. 33, pp. 894–897 (1988).

FIG. 1 shows a plot of the spectral characteristics of excised skin, with no associated fat 101, pure collagen 102, and beef fat 103. The processed second derivative is used to compare the contributions of fat and collagen with the excised skin, mainly consisting of collagen and water.

Interaction Between Light and Human Skin

When a beam of light beam is directed onto the skin surface, a part of it is reflected while the remaining part penetrates the skin. The proportion of reflected light energy is strongly dependent on the angle of incidence. At nearly perpendicular incidence, about 4% of the incident beam is reflected due to the change in refractive index between air ($\eta_D=1.0$) and dry stratum corneum ($\eta_D=1.55$). For normally incident radiation, this "specular reflectance" component may be as high as 7%, because the very rigid and irregular surface of the stratum corneum produces off-normal angles of incidence. Regardless of skin color, specular reflectance of a nearly perpendicular beam from normal skin is always between 4–7% over the entire spectrum from 250–3000 nm. See R. Scheuplein, *J. Soc. Cosmet. Chem.*, v. 15, pp. 111–122 (1964). Only the air-stratum corneum border gives rise to a regular reflection. Results from a previous study indicate that the indices of refraction of most soft tissue (skin, liver, heart, etc) lie within the 1.38–1.41 range with the exception of adipose tissue, which has a refractive index of approximately 1.46. See J. Parrish, R. Anderson, F. Urbach, D. Pitts, *UV-A: Biologic Effects of Ultraviolet Radiation with Emphasis on Human Responses to Longwave Ultraviolet*, New York, Plenum Press (1978). Therefore, these differences in refractive index between the different layers of the skin are too small to give a noticeable reflection. See Ebling, *supra*. The differences are expected to be even more insignificant when the stratum corneum is hydrated, owing to refractive index matching.

The 93–96% of the incident beam that enters the skin is attenuated due to absorption or scattering within any of the layers of the skin. These two processes taken together essentially determine the penetration of light into skin, as well as remittance of scattered light from the skin. Diffuse reflectance or remittance is defined as that fraction of incident optical radiation that is returned from a turbid sample. Absorption by the various skin constituents mentioned above account for the spectral extinction of the beam within each layer. Scattering is the only process by which the beam may be returned to contribute to the diffuse reflectance of the skin. Scattering results from differences in a medium's refractive index, corresponding to differences in the physical characteristics of the particles that make up the medium. The spatial distribution and intensity of scattered light depends upon the size and shape of the particles relative to the wavelength, and upon the difference in refractive index between the medium and the constituent particles.

The scattering coefficient of biological tissue depends on many uncontrollable factors, which include the concentration of interstitial water, the density of structural fibers, and the shapes and sizes of cellular structures. Scattering by collagen fibers is of major importance in determining the penetration of optical radiation within the dermis. See F. Bolin, L. Preuss, R. Taylor, R. Ference, *Appl. Opt*, v. 28, pp. 2297–2303 (1989). The greater the diffusing power of a medium, the greater will be the absorption related to multiple internal reflections. Therefore, reflectance values measured on different sites on the same person, or from the same site on different people, can differ substantially even when the target absorber is present in the same concentration. These differences can be attributed to gender, age, genetics, disease, and exogenous factors due to lifestyle differences. For example, it is known that skin thickness in humans is greater in males than females, whereas the subcutaneous fat thickness is greater in females. The same group reports that collagen density, the packing of fibrils in the dermis, is higher in the forearms of males than females. See S Schuster, M. Black, E. McVitie, *Br. J. Dermatol*, v. 93, pp. 639–643, (1975).

Dynamic Properties of the Skin

While knowledge of and utilization of the properties of the skin, high instrument sensitivity, and compensation for inherent nonlinearities are all vital for the application of non-invasive technologies to noninvasive tissue analyte measurement, an understanding of biological and chemical mechanisms that lead to time dependent changes in the properties of skin tissue is equally important and, yet, largely ignored. At a given measurement site, skin tissue is often assumed to be static except for changes in the target analyte and other interfering species. However, variations in the physiological state and fluid distribution of tissue profoundly affect the optical properties of tissue layers and compartments over a relatively short period of time. Such variations are often dominated by fluid compartment equalization through water shifts and are related to hydration levels and changes in blood analyte levels.

Total body water accounts for over 60% of the weight of the average person and is distributed between two major compartments: the intracellular fluid (two-thirds of total body water) and the extracellular fluid (one-third of total body water). See A. Guyton, J. Hall, *Textbook of Medical of Physiology*, $9^{th}$ ed., Philadelphia, W. B. Saunders Company (1996)]. The extracellular fluid in turn is divided into the interstitial fluid (extravascular) and the blood plasma (intravascular). Water permeable lipid membranes separate the compartments and water is transferred rapidly between them through the process of diffusion, in order to equalize the concentrations of water and other analytes across the membrane. The net water flux from one compartment to another constitutes the process of osmosis and the amount of pressure required to prevent osmosis is termed the osmotic pressure. Under static physiological conditions the fluid compartments are at equilibrium. However, during a net fluid gain or loss as a result of water intake or loss, all compartments gain or lose water proportionally and maintain a constant relative volume.

An important mechanism for distributing substances contained in blood serum that are needed by the tissues, water and glucose, for example, is through the process of diffusion.

It can be seen that Fick's Law of diffusion drives the short-term intra-/extra vascular fluid compartment balance. The movement of water and other analytes from intravascular to extravascular compartments occurs rapidly as molecules of water and other constituents, including glucose, in constant thermal motion, diffuse back and forth through the capillary wall. On average, the rate at which water molecules diffuse through the capillary membrane is about eighty times greater than the rate at which the plasma itself flows linearly along the capillary. In the Fick's Law expression, the actual diffusion flux, $I_{OA}$, is proportional to the concentration gradient, $dC/dx$ between the two compartments and the diffusivity of the molecule, $D_A$ according to the equation $$I_{QA} = -D_A\left(\frac{dC}{dx}\right) \quad (1)$$

Short-term increases (or decreases) in blood glucose concentrations lead to an increase (or decrease) in blood osmolality (number of molecules per unit mass of water). Fluid is rapidly re-distributed accordingly and results in a change in the water concentration of each body compartment. In the case of hyperglycemia, the osmotic effect leads to a movement of extravascular water to the intravascular space compartment where glucose concentrations are higher. At the same time, glucose is transported from the intravascular space to the extravascular compartment in an effort to equilibrate the osmolality of the two compartments. Conversely, a decrease in blood glucose concentration leads to a movement of water to extravascular space from the intravascular compartment along with the movement of glucose from the extravascular space into the intravascular space.

Because the cell membrane is relatively impermeable to most solutes but highly permeable to water, whenever there is a higher concentration of a solute on one side of the cell membrane, water diffuses across the membrane toward the region of higher solute concentration. Large osmotic pressures can develop across the cell membrane with relatively small changes in the concentration of solutes in the extracellular fluid. As a result, relatively small changes in concentration of impermeable solutes in the extracellular fluid, such as glucose, can cause tremendous changes in cell volume.

Sampling Error

Noninvasive measurement of tissue properties and analytes, such as blood glucose concentration, may employ NIR spectroscopic methods. S. Malin, T. Ruchti, U.S. Pat, No. 6,280,381, supra, describes a system for noninvasively predicting blood glucose concentrations in vivo, using NIR spectral analysis. Such NIR spectroscopy-based methods utilize calibrations that are developed using repeated in vivo optical samples of the same tissue volume. These successive measurements must yield a substantially repeatable spectrum in order to produce a usable calibration. As herein described, the heterogeneous and dynamic nature of living human skin leads to sampling uncertainty in the in vivo measurement. Sampling differences can arise due to variable chemical composition and light scattering properties in tissue. As an example: because glucose is not uniformly distributed in tissue, a variation in the volume of tissue sampled is likely to lead to a variation in the strength of the glucose signal, even though glucose concentration in the tissue or blood remains constant. Variation in the repeated placement of the optical probe used for sampling at the measuring surface site can lead to sampling errors in two separate ways: first, variations in the location of the probe can cause a different tissue volume to be sampled, and second, varying the amount of pressure applied by the probe on the tissue can alter the optical scattering by the tissue, thereby changing the sampled tissue volume. A change in optical sampling may lead to a variation in the spectral signal for a target analyte even though the concentration of the analyte in the blood or tissue remains unchanged. Furthermore, air gaps between the surface of the optical probe and the surface of the tissue being sampled give rise to variable surface reflection. Variable surface reflection leads to a variable light launch into the tissue that in turn gives rise to an increase in nonlinear nature of the spectral measurements. Certainly, a variable nonlinear measurement would be very difficult to calibrate.

Various systems for guiding and coupling optical probes are known. For example, M. Rondeau, *High Precision Fiberoptic Alignment Spring Receptacle and Fiberoptic Probe*, U.S. Pat. No. 5,548,674; Aug. 20, 1996 and R. Rickenbach and R. Boyer, *Fiber Optic Probe*, U.S. Pat. No. 5,661,843; Aug. 26, 1997 both disclose fiber optic probe guides utilizing ferrules through which a fiber optic cable or thread is longitudinally threaded. Both devices are connectors that couple fiber optic cables or threads to receptacles in various forms of medical equipment, or to other fiber optic cables. Neither device provides a means for repeatably coupling a fiber optic probe to a tissue measurement site.

T. Kordis, J. Jackson, and J. Lasersohn, *Systems Using Guide Sheaths for Introducing, Deploying and Stabilizing Cardiac Mapping and Ablation Probes*, U.S. Pat. No. 5,636,634; Jun. 10, 1997 describe a system that employs catheters and guide sheaths to guide cardiac mapping and ablation probes into the chambers of the heart during surgery or diagnostic procedures. The Kordis teachings are directed to surgical methods for the heart, and have nothing to do with optical sampling of tissue in vivo.

Furthermore, the apparatus of Kordis, et al. would not be suitable for repeatably coupling an optical probe to a tissue measurement site.

M. Kanne, *Laser Mount Positioning Device and Method of Using the Same*, U.S. Pat. No. 5,956,150; Sep. 21, 1999 describes a method for using an illumination device, such as a laser to align two components during an assembly process. The Kanne teachings are directed to a manufacturing process rather than optical sampling of tissue in vivo. The Kanne device does not provide any means for repeatably placing a probe guide at a tissue measurement site. It also has no way of monitoring the surface temperature at a tissue measurement site, or of minimizing surface temperature fluctuations and accumulation of moisture at a tissue measurement site.

D. Kittell, G. Hayes, and P. DeGroot, *Apparatus for Coupling an Optical Fiber to a Structure at a Desired Angle*, U.S. Pat. No. 5,448,662, Sep. 5, 1995 disclose an optical fiber support that is coupled to a frame for positioning an optical fiber at a desired angular position. As with the prior art previously described, the teachings of Kittell, et al. have nothing to do with optical sampling of tissue in vivo. Furthermore, the disclosed device allows an operator to immobilize an optical fiber so that it is maintained in a fixed position, but it does not offer a means of repeatably coupling a fiber optic probe to a tissue measurement site. It also has no way of monitoring the surface temperature at a tissue measurement site, or of minimizing accumulated moisture and temperature fluctuations at the site.

R. Messerschmidt, *Method for Non-Invasive Blood Analyte Measurement with Improved Optical Interface*, U.S. Pat. No. 5,655,530, Aug. 12, 1997 discloses an index-matching medium to improve the interface between a sensor probe and a skin surface during spectrographic analysis. Messerschmidt teaches a medium containing perfluorocarbons and chlorofluorocarbons. Since they are known carcinogens, chlorofluorocarbons (CFC's) are unsuitable for use in preparations to be used on living tissue. Furthermore, use of CFC's poses a well-known environmental risk. Additionally, Messerschmidt's interface medium is formulated with substances that would be likely to leave artifacts in spectroscopic measurements.

There exists, therefore, a need in the art for a means of achieving the precise optical sampling necessary for developing noninvasive calibrations for measuring tissue analytes. A solution to the problem of controlling optical sampling during a noninvasive measurement needs to address several challenges posed by the structural characteristics and dynamic properties of living tissue, in particular, skin:

Controlling surface reflection due to optical aberrations in surface coupling and stretching of the surface tissue;

Controlling variations in tissue volume sampled due to imprecise placement; and variable stretching of dermal collagen, leading to sampling volume uncertainty;

Correcting measurement bias related to water pooling in the tissue resulting from pressure on the area in the vicinity of the measurement site from instrumentation or placement guides; and Stabilizing hydration of surface tissue.

It would be desirable to provide a placement guide for an optical probe that coupled the probe to a tissue measurement site for in vivo optical sampling of the tissue. It would also be desirable to provide a means of assuring that the same tissue sample volume may be repeatably sampled, thus eliminating sampling errors due to mechanical tissue distortion and probe placement. It would also be desirable to provide a way to minimize temperature fluctuations and stabilize stratum corneum moisture content at the tissue measurement site, thus eliminating further sources of sampling error. It would also be highly advantageous to provide an optical coupling medium to provide a constant interface between an optical probe and the skin at a tissue measurement site that is non-toxic and non-irritating and that doesn't introduce error into spectroscopic measurements. Additionally, it would be advantageous to provide a means of monitoring surface temperature at the tissue measurement site, therefore assuring that the temperature remains constant across repeated optical samples. Finally, it would be advantageous to provide a means for correcting the tissue sampling bias that results from the uncertainty inherent to the mechanical attachment process used to install the placement guide at the measurement site.

SUMMARY OF THE INVENTION

The invention provides an optical sampling interface system that minimizes and compensates error resulting from sampling variation and/or state fluctuations at a measurement site during optical tissue sampling and subsequent analyte measurement by spectroscopic means.

An optical probe placement guide facilitates repeatable location accuracy on the surface of a tissue measurement site with a minimal and repeatable degree of tissue distortion and displacement. The major structural component of the probe placement guide is a mount having an aperture, into which the optical probe is received during use. In addition to improving the precision of probe placement during the course of multiple measurements, the guide aperture induces the formation of a tissue meniscus, created by the pooling of epidermal water in the guide aperture due to the relative difference in the contact pressure at the guide adhesion surface and the guide aperture, where no part of the guide contacts the tissue. The formation of the tissue meniscus minimizes interference due to surface irregularities and controls variation in the volume of tissue sampled.

An occlusive element placed over the tissue meniscus isolates the tissue meniscus from environmental fluctuations, thus stabilizing the degree of hydration of the tissue meniscus and thereby stabilizing surface tension of the tissue meniscus. An optical coupling medium placed on the surface tissue at the tissue measurement site eliminates sampling errors due to air gaps between the skin surface and the optical probe.

A measurement and bias correction element applies a bias correction to spectral measurements, and the associated analyte measurement. Such bias corrections are performed identically for all data taken over the course of one guide placement. When the guide is removed and replaced, a new bias correction is determined for all subsequent data taken with the second guide placement.

Additionally, each of the separate elements of the invented system can be individually deployed, as standalone solutions to counter various sources of measurement error. Thus, the probe placement guide, independent of the other elements of the system, provides a significant reduction in sampling error; the occlusive element provides a significant reduction in measurement error due to state fluctuations at the surface of the measurement site; and the correction algorithm can be applied to spectral measurements in settings lacking the other elements of the system.

DETAILED DESCRIPTION

In spectroscopic analysis of living tissue, it is often necessary to optically sample the same tissue volume repeatedly though the use of an optical probe; for example while developing a noninvasive calibration for measuring one or more tissue analytes, and subsequently, when taking measurements for the actual analyte measurement. Sampling errors can be introduced into these measurements because of the difficulty of repeatedly placing the optical probe at the precise location used in preceding measurements, and repeatably producing the same nominal degree of tissue distortion and displacement. With each small variation in the location of the probe, or variations in the amount of pressure resulting from the repeated probe contact events, a slightly different tissue volume is sampled, thereby introducing sampling errors into the measurements. The invention provides an optical sampling interface system that eliminates or minimizes factors that account for sampling error.

Probe Placement Guide

A system is described herein that provides superior sampling precision of the target tissue volume through the use an optical probe placement guide that is removably attached to the tissue site to achieve the goal of highly repeatable probe placement at a targeted tissue measurement site. A key characteristic of the guide is that it provides a means for registering the location of the targeted tissue volume with respect to the optical probe such that a particular tissue volume is precisely sampled by the optical system. Registration refers to providing feedback regarding the position of the optical probe relative to a target location on the tissue. The means for registering between the guide and the optical probe may be mechanical, optical, electrical or magnetic. In addition, the guide includes an aperture into which the optical probe is received. The aperture serves several purposes including those of:

a mechanical registration point;
a means for creating a stable tissue meniscus; and
an opening for receiving an occlusion plug so that the surface state of the tissue at the measurement site may be stabilized between measurements.

Figure 1:
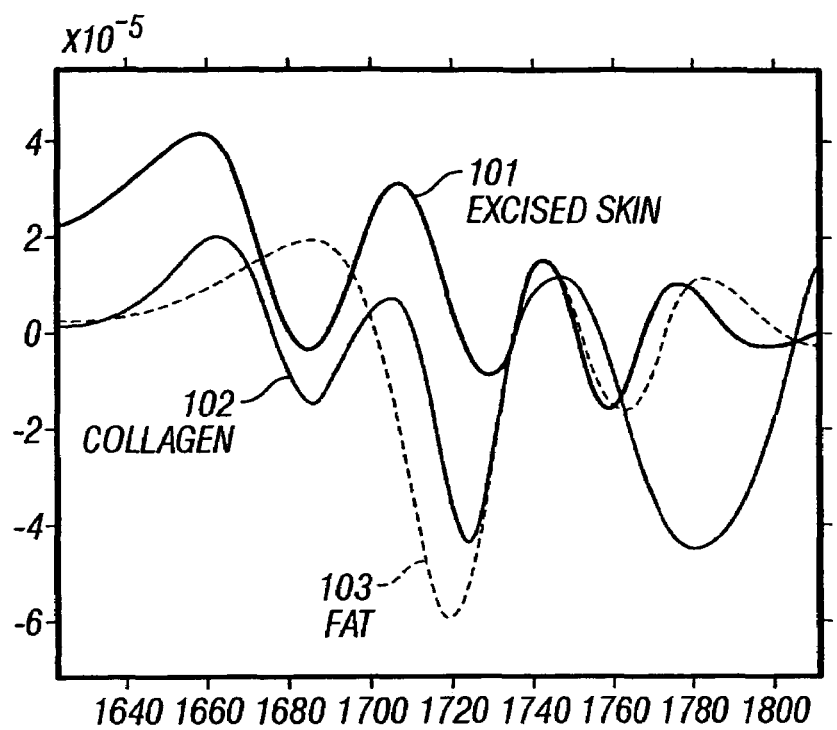
FIG. 1 shows second derivative absorbance spectra of excised human skin, pure fat and pure collagen.
Figure 2:
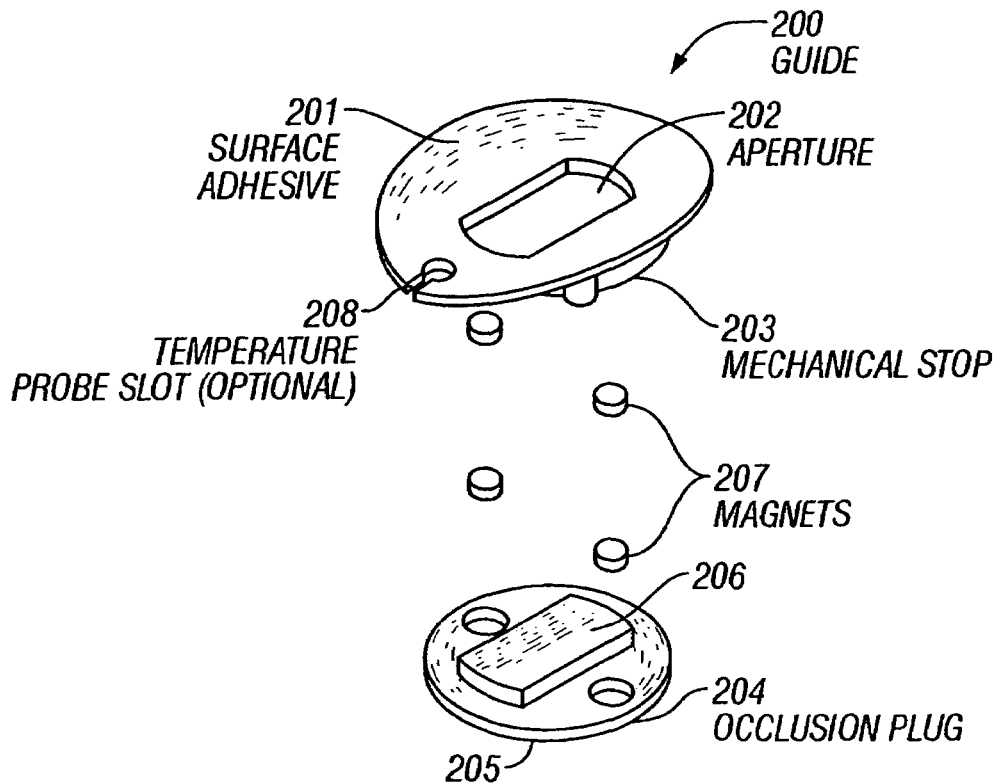
FIG. 2 shows an optical probe placement guide according to the invention.

In the preferred embodiment, shown in FIG. 2, the guide 200 is oval and contoured to approximate the surface of the sampled tissue site, for example, the volar (that corresponding to the palm of the hand) or dorsal surface of the forearm. However, other shapes are used for other locations of the body such as the hand, the earlobe, the leg, the abdomen, the upper arm region and the fingers. The design of the guide is intended to allow for comfortable and unobtrusive use without application of significant mechanical energy to the sampled tissue site. In the current embodiment, the guide is composed of a rigid polymer, allowing for the creation of a stable tissue meniscus. However, other materials providing the requisite combination of rigidity and light weight, such as lightweight metals, would also be suitable.

Attachment of the guide to the tissue site may be by means of an adhesive layer 201 on the contact surface of the guide 200. The adhesive layer may be applied at the time of manufacture, or it may be applied to the guide prior to usage. Generally, the adhesive covers the entire contact surface of the guide, that surface of the guide that is in contact with the skin area adjacent to and surrounding the tissue measurement site. Additionally, other attachment means are suitable such as straps, suction, or armbands. The guide is attached to the tissue site at the beginning of a measurement period. Typically this period is the beginning of a particular day after a previously used guide has been removed. In the preferred embodiment, the method of attachment is to place the guide 200 onto a noninvasive measurement device with the adhesive layer in place and exposed. The tissue measurement site is then placed onto the guide with a rough registration through an arm cradle or elbow and wrist supports. During this first placement, the guide becomes affixed to the tissue site.

The guide 200 allows for the distribution of mechanical energy transferred from the instrument to the arm over a greater area around the measurement site. However, in applications involving a portion of the body subject to deformation or movement, the guide may be composed of a flexible material, such as a flexible polymer, that provides for a stabilization of the measurement site and deformation of the underlying tissue without applying undue force to the targeted tissue volume.

The guide has an aperture 202, into which an optical probe is received. The sizes and shapes of the optical probe and the guide aperture 202 are matched to each other such that when the optical probe is received by the guide, it fits snugly and provides a mechanical registration in the x-y plane relative to the tissue measurement site. To avoid over-penetration of the optical probe into the tissue and to promote a repeatable pressure between the optical probe and the tissue, the guide and the optical probe are equipped with mechanical stops 203 that limit and control the penetration of the optical probe into the tissue (the z-direction). The weight of the tissue is transferred to the optical probe through the mechanical stop 203 and thereby reduces the pressure at the tissue measurement site.

The guide is equipped with a slot 208 for the optional insertion of a temperature probe. This feature is particularly useful during the calibration phase for monitoring of skin temperature.

Measurement Site Occlusion

When the tissue site is not being Interfaced to the optical probe an occlusion plug 204 is normally inserted into the aperture 202. The occlusion plug penetrates into the aperture to the same extent as the optical probe and thereby creates a stable tissue state by simulating the contact energy of the optical probe. As discussed previously, the occlusion plug is composed of a material that provides a hydration barrier, thus promoting the full and stable hydration of the stratum corneum. In the preferred embodiment, the plug is composed of the same material as the guide and possess a mechanical stop 205 to control the penetration into the tissue site. The size of the portion of the plug that is inserted into the aperture 206 is matched to the portion of the optical probe that is received by the guide aperture 202. Attachment of the plug to the guide may be through the use of one or more magnets located in both the guide and plug assemblies 207. However, other methods of attachment may be used, such as VELCRO, also known as hook and loop tape; adhesives and snaps. Alternately, the plug can be composed of a material that is elastic in nature and is kept in place by virtue of its tight fit Into the guide aperture. Also, the plug can be a hydrophobic material, such as cellophane.

From the foregoing, one of ordinary skill in the art will recognize that an important aspect of the optical sampling system is the maintenance of an optimal level of hydration of the surface tissue at the measurement site for enhancement of the optical signal, sample reproducibility, and suppression of surface reflectance. As previously described, the preferred embodiment of the hydration mechanism is by occlusive blockage of trans-epidermal water loss (TEWL). This blockage ensures a steady state hydration as water diffusing from interior tissue is trapped in the stratum corneum. Attainment of high hydration levels reduces the water concentration gradient that provides the driving force for this trans-epidermal water movement. Thus, the above described occlusive plug fits snugly into the guide aperture during periods between measurements, acting to insulate the tissue in the guide aperture from trans-epidermal water loss and the environmental effects of temperature and humidity that are known to influence the stratum corneum hydration state. In addition to the preferred embodiment just described, in alternate embodiment, wrapping a flexible polymer sheet (an occlusion patch) around the measurement site may also be used to attain a highly hydrated state via occlusion.

Other solutions to the problem of maintaining hydration of the stratum corneum, consistent with the spirit and scope of the invention are possible, including, but no limited to:

a vapor barrier or semi-permeable membrane (for example, GORE-TEX, manufactured by W. L. Gore and Associates of Newark DE as the mount) in the form of a wrap or a patch configured to cover the site target for measurement. In this latter embodiment the "patch" is affixed to the tissue site through an adhesive or other attachment mechanism such as a strap or a wrap;

non-occlusive mechanisms for hydration of the stratum corneum may also be used, including:

an application of water that is pneumatically driven into the skin;

ultrasound energy applications to accelerate passive occlusion; and topical application of skin toners and other water/solute mixtures such as alpha hydroxy acid solutions that serve to drive water and solute into the dry outer skin layer.

topical analgesic formulations that enhance and/or stimulate local circulation at the measurement site leading to an improvement in surface hydration.

The mechanisms for achieving stratum corneum hydration may also be used in coupled treatments. For example: Skin toner solution or an ultrasound energy application may be used in conjunction with an occlusive plug.

After an initial measurement is made, as described above, subsequent measurements are made by simply placing the tissue site onto the noninvasive measurement device (after removing the occlusion plug) and allowing the guide to provide mechanical registration. After the optical tissue measurement is performed, the tissue is taken away from the device and the occlusion plug is re-inserted.

Optical Registration

In an alternate embodiment, the guide provides a means for optical registration. In this embodiment, reflectors or light sensitive elements are placed onto the guide. The optical probe assembly is equipped with light sources and several detectors that allow the position of the guide to be accurately assessed, in either two or three dimensions. In a first configuration, two dimensions (x,y) are assessed and a mechanical stop is used to control the third dimension. In a second configuration, the location of the guide is optically assessed in all three dimensions (x,y,z). Because the position of the guide is constant with respect to the targeted tissue volume, the positional assessment provides accurate information regarding the location of the targeted tissue volume with respect to the optical probe. The registration information provided by such assessment is used to place the tissue site onto the optical probe, or vice versa, through any of the following means:

an operator or user is given a visual or audible signal indicating how to move the tissue site with respect to the optical probe;

a mechanical positioning system is used to position the tissue measurement site with respect to the optical probe; or a mechanical positioning system is used to position the optical probe onto the tissue measurement site.

One skilled in the art will appreciate that a magnetic sensing system can also be readily applied for assessment of the location of the guide with respect to the tissue measurement site.

In addition to improving the precision of the probe placement event during the course of multiple measurements, the guide aperture induces the formation of a tissue meniscus, an upward bulge of tissue into the optical probe aperture. The tissue meniscus, a pooling of subsurface water in the guide aperture resulting from a relative difference in the contact pressure at the guide adhesion surface and the guide aperture, both provides for limitation of the penetration of the probe into the tissue and guarantees a highly compliant and energy absorbing contact event.

The hydrostatic pressure within the tissue in the aperture is greater than that on the nude (guideless) tissue sample. This increased hydrostatic pressure absorbs energy translated to the tissue when the probe contacts the tissue, thus limiting the resulting distortion of dermal collagen tissue. Distortion of dermal collagen has a strong effect on the tissue optical properties and thus the sampled tissue volume. In order to achieve this correction, the termination of the optical probe should be flush with the contact surface at the tissue measurement site when the optical probe is fully seated.

Optical Coupling Medium

Figure 3:
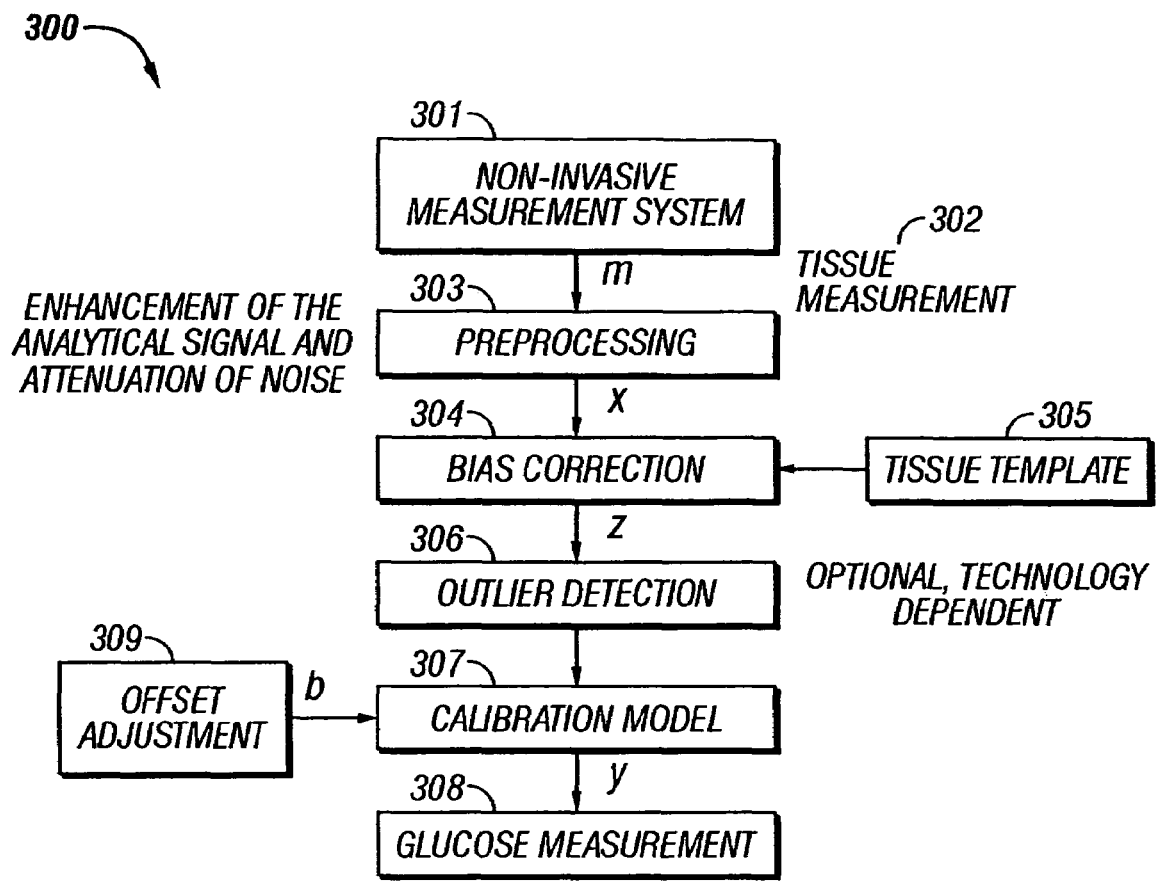
FIG. 3 provides a block diagram of a measurement and bias correction system according to the invention.
Figure 4:
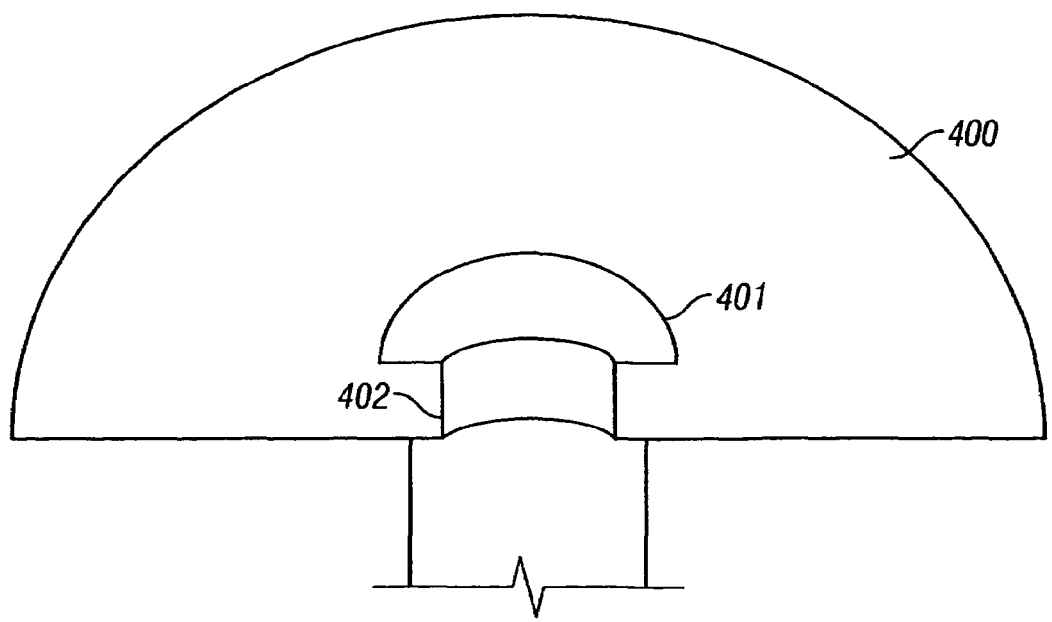
FIG. 4 shows an optical probe and a tissue measurement site optically coupled by a layer of an optical coupling fluid according to the invention.

The interface between the optical probe and the skin surface at the tissue measurement site can also be a significant source of sampling error. Since the underlying tissue is not homogenous, the surface skin at the tissue measurement site may be uneven, with frequent irregularities. Coupling the relatively smooth surface of the optical probe with the irregular skin surface leads to air gaps between the two surfaces. The air gaps create an interface between the two surfaces that adversely affects the measurement during optical sampling of tissue. As shown in FIG. 3, an amount of an optical coupling medium such as an optical coupling fluid 401 between the optical probe 402 and the skin of the tissue measurement site 400 eliminates such gaps.

Preferably, the optical coupling fluid:

is spectrally inactive;

is non irritating and nontoxic; and has low viscosity for good surface coverage properties.

and has poor solvent properties with respect to leaching fatty acids and oils from the skin upon repeated application.

It is possible to achieve such characteristics by selecting the active components of the optical coupling fluid from the class of compounds called perfluorocarbons, those containing only carbon and fluorine atoms. Nominally limiting chain length to less than 20 carbons provides for a molecule having the requisite viscosity characteristics. The molecular species contained in the perfluorocarbon coupling fluid may contain branched or straight chain structures. A mixture of small perfluorocarbon molecules contained in the coupling fluid as polydisperse perfluorocarbons provides the required characteristics while keeping manufacturing costs low.

In a preferred embodiment, the optical coupling fluid is a perfluoro compound such as those known as FC-40 and FC-70, manufactured by 3M Corporation. Such compounds are inactive in the Near IR region, rendering them particularly well suited for optical sampling procedures employing Near IR spectra. Additionally, they have the advantage of being non-toxic and non-irritating, thus they can come into direct contact with living tissue, even for extended periods of time, without posing a significant health risk to living subjects. Furthermore, perfluoro compounds of this type are hydrophobic and are poor solvents; therefore they are unlikely to absorb water or other contaminants that will adversely affect the result during optical sampling. It is preferable that the optical sampling fluid be formulated without the addition of other substances such as alcohols or detergents, which may introduce artifacts into the optical sample. Finally, the exceptional stability of perfluoro compounds eliminates the environmental hazard commonly associated with chlorofluorocarbons.

Other fluid compositions containing perfluorocarbons and chlorofluorocarbons are also suitable as optical coupling fluids: for example a blend of 90% polymeric chlorotrifluoroethylene and 10% other fluorocarbons would have the desired optical characteristics. Chlorotrifluorethene could also be used. While these compositions have the desired optical characteristics, their toxicity profiles and their solvent characteristics render them less desirable than the previously described perfluoro compounds.

Additionally, other fluid media are suitable for coupling of an optical probe to a tissue measurement site, for example, skin toner solutions or alpha hydroxy-acid solutions.

During use, a quantity of optical sampling fluid is placed at the interface of the tissue measurement site and the fiber optic probe so that the tissue measurement site and the fiber optic probe may be tightly optically coupled without leaving any air spaces between the two surfaces. In practice, one convenient way of placing the quantity of the optical sampling fluid at the interface between the tissue measurement site and the probe is to place a small amount of the fluid on the skin surface prior to placing the fiber optic probe, although it is easier to place it on the fiber-optic probe.

Furthermore, certain non-fluid media having the requisite optical characteristic of being near-IR neutral are also suitable as optical coupling media, for example, a GORE-TEX membrane interposed between the probe and the surface of the measurement site, particularly when used in conjunction with one of the fluid media previously described.

Bias Correction

Finally, a bias correction is preferably made to the measurement to account for variations in the size of the meniscus caused by the guide installation. These bias corrections are applied to the processed spectral measurement and to the predicted analyte value just prior to prediction An embodiment of a bias correction system 300 associated with the guide apparatus is summarized in FIG. 3. A non-invasive measurement system 301 provides a "tissue measurement" (302), $m \in \Re^{1 \times N}$ where N corresponds to the dimensionality of the measurement. In the preferred embodiment, m refers to the intensity spectrum of the tissue sample represented by the intensity at N wavelengths (or wavelength ranges or selected wavelengths) selected from a wavelength range, for example 700–2500 nm. In the preferred embodiment, a background or reference, $m_o$, is used to standardize or normalize the tissue measurement according to the calculation $$a = -\log_{10}\left(\frac{m}{m_o}\right) \tag{2}$$

where $m_o$ is an estimate of light incident on the sample, m is an intensity spectrum of light detected and a is analogous to an absorbance spectrum containing quantitative information that is based on the known interaction of the incident light with components of the body tissue. Alternately, the tissue measurement, m, can be used directly instead of a.

The standardized tissue measurement, a, is preferably preprocessed 303 to attenuate noise and to reduce the interference related to surface reflectance, tissue volume distortion and instrumental effects to produce the processed tissue measurement, x. In the preferred embodiment the preprocessing steps include calculating the first derivative, selecting specific wavelengths and wavelength regions specific to the analyte of interest and scatter correction (e.g., multiplicative scatter correction).

A bias correction step 304 follows the preprocessing steps defined above through the determination of the difference between the preprocessed estimated tissue background—the tissue template 305, and x through $$z = x - (cx_t + a) \tag{3}$$

where x is the preprocessed tissue measurement or the selected set of features, $x_t$ is the estimated background or tissue template associated with the current guide placement, and c and d are slope and intercept adjustments to the tissue template. After each guide placement, the tissue template 305 is determined through one or more tissue measurements (after preprocessing) and a data selection criterion (for example, by selecting only tissue measurements that resemble each other closely and averaging them). In the preferred embodiment, $x_t$ is calculated from a single tissue measurement that is collected after an equalization period following the placement of the guide and c=1 and d=0. This process is referred to as "bias correction" and involves both:

the collection of one or more tissue measurements that are processed to form a tissue template; as well as an associated set of reference analyte values determined from a primary analyte measurement source.

For example, in the case of near-infrared measurement of glucose, the reference analyte values are determined from an electrochemical analysis of blood draws. The analyte values are combined, according to the same strategy as that used to create the tissue template to form an analyte measurement bias adjustment 309, b, through the equation $$\hat{y} = g(z) + b \tag{4}$$

where $g: \Re^M \to \Re^1$ is a calibration model 307 used to map z to an estimate of the target analyte 308. The model is determined from a calibration set of exemplary paired data points each consisting of a pre-processed and bias corrected tissue measurement (z) and an associated reference analyte value (y) determined from an analysis of a blood or interstitial fluid sample. According to this process, blood, serum, plasma, or interstitial draws are taken from a tissue site that is either near the sensor sample site or has been designed/determined to reflect the sample site. For example, when non-invasive near-infrared measurements for the purpose of glucose measurement are taken for calibration on the forearm, it is possible in some individuals to collect a capillary blood draw from the same forearm or an alternate site such as opposite forearm. Alternately, rather than using blood draws, it is beneficial in some instances to use interstitial glucose values rather than capillary glucose values. The method for designing the structure of g is through the process of system identification [L. Ljung, *Systems Identification: Theory for the User*, 2d. ed., Prentice Hall (1999)]. The model parameters are calculated using known methods including multivariate regression or weighted multivariate regression [N. Draper, H. Smith, *Applied Regression Analysis*, 2d. ed., John Wiley and Sons, New York (1981)], principal component regression [H. Martens, T. Naes, *Multivariate Calibration*, John Wiley and Sons, New York (1989)], partial least squares regression [P. Geladi, B. Kowalski, *Partial least-squares regression: a tutorial*, Analytica Chimica Acta, 185, pp. 1–17, (1986)], or artificial neural networks [S. Haykin, *Neural Networks: A Comprehensive Foundation*, Prentice Hall, Upper Saddle River N.J. (1994)]. Calibration data must also be bias corrected if data contains subsets associated with different guide placement events.

Optionally, the bias corrected tissue measurements undergo an outlier detection step 306. As indicated in FIG. 3, the necessity for outlier detection, and the form of an outlier detection procedure are dependent on the sampling technology employed. Outlier detection provides a method of detecting invalid measurements through spectral variations that result from problems in the instrument, poor sampling of the subject or a subject outside the calibration set. One method of detecting outliers is through a principal component analysis and an analysis of the residuals.

EXEMPLARY APPLICATIONS

Example 1

A study was performed to examine the difference in spectral variation between several different near-infrared sampling treatments on a single subject. Near-infrared spectra were collected using a custom built scanning near-infrared spectrometer that collected intensity spectra in diffuse reflectance over the wavelength range 1100–1950 nm. The spectral sampling interval was one nanometer and the signal-to-noise ratio at the peak intensity was approximately 90 dB. The detector used in the study was Indium-Gallium-Arsenide (InGaAs) and the optical configuration consisted of a simple fiber optic interface to the skin with a small (<2 mm) distance between the illumination and detection fibers. Reference spectra were recorded before each sample measurement by scanning a 99% SPECTRALON reflectance material provided by LABSHPERE of North Sutton N.H. The absorbance spectrum was calculated through Equation (2), supra.

Approximately twenty near-infrared absorbance spectra were collected on the subject's forearm using the following treatments:
1. Baseline measurements using only elbow and wrist supports to guide the patient's arm placement;
2. Measurements were taken using the preferred embodiment of the guide positioning system herein described, without occlusion of the measurement site; and
3. Both the guide positioning system and the disclosed method of occlusion (a plug in the aperture of the guide).

Figure 5:
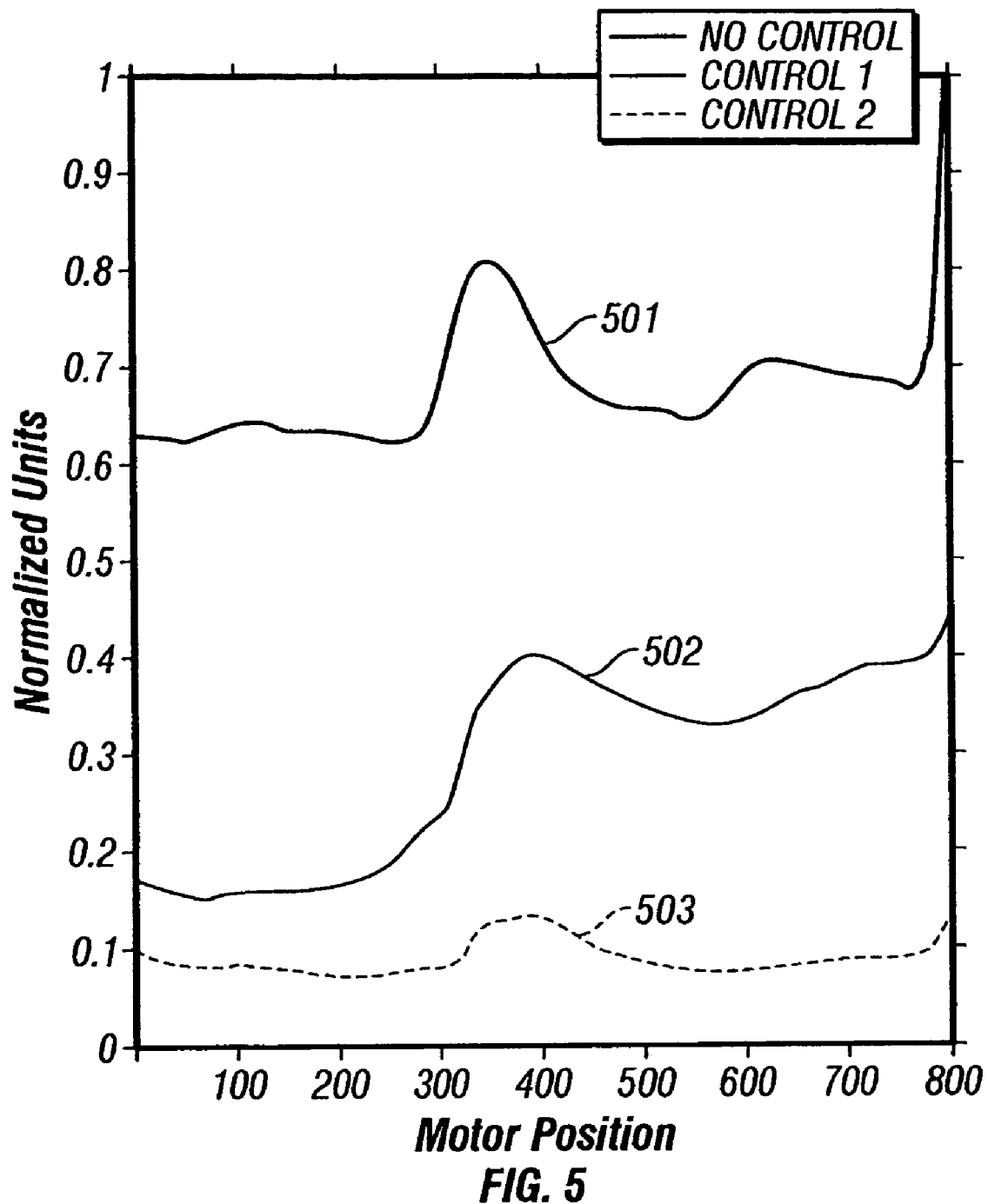
FIGS. 5–7 show plots of measurement variation attributable to sampling error without and with the invention.

Before the collection of each spectrum, the subject's arm was replaced on the optical probe. Analysis of the data was performed on each of the three data subsets described above and consisted of calculating the root mean square variation at each motor position of the spectrometer. A plot of the normalized RMS variation versus motor position is given in FIG. 5. As shown, the plot 501 of RMS variation without the guide positioning system shows relatively more sample variation. As the plots 502, 503, respectively, indicate, the relative variation related to replacement of the subjects arm on the optical probe is reduced by utilization of the guide (Control 1) and still further reduced through the addition of site occlusion (Control 2).

Example 2

Figure 6A:
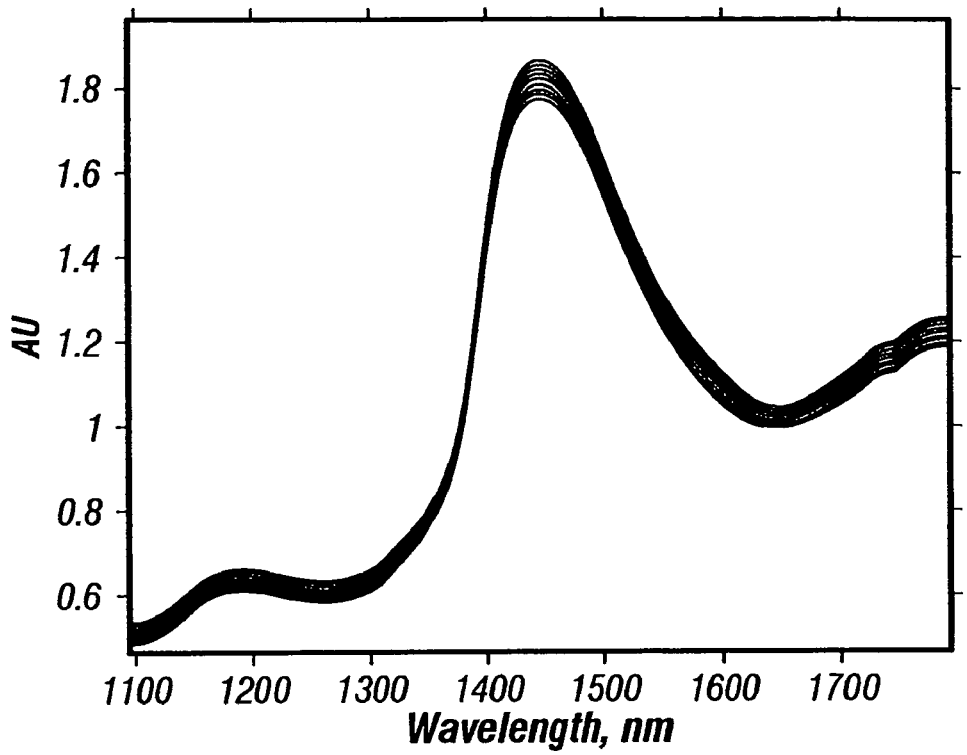
Figure 6B:
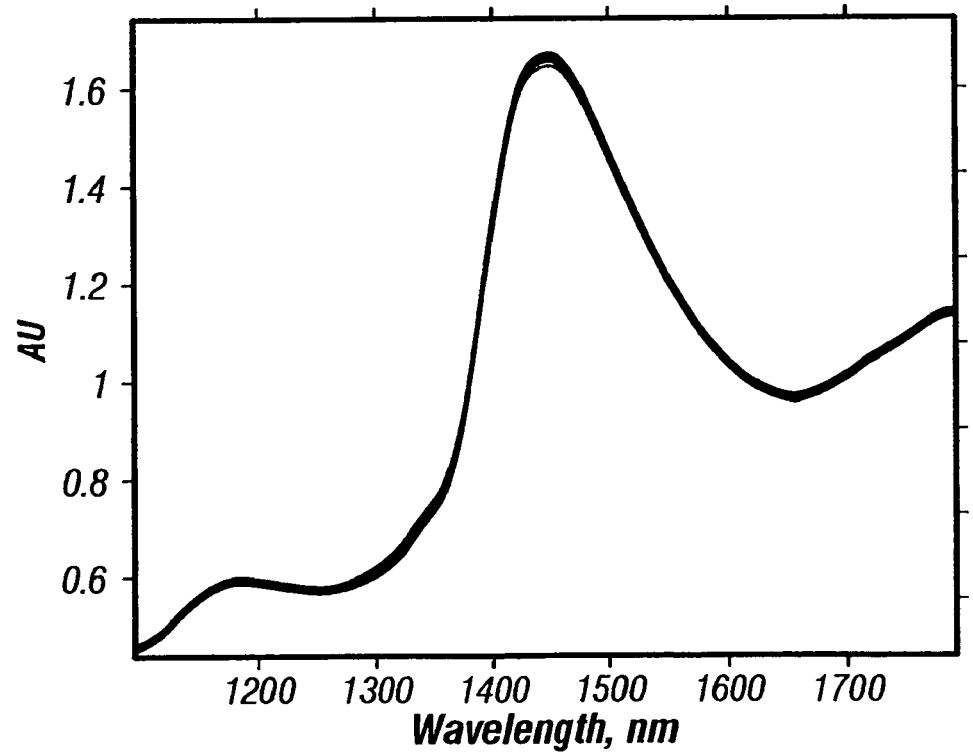
Figure 7A:
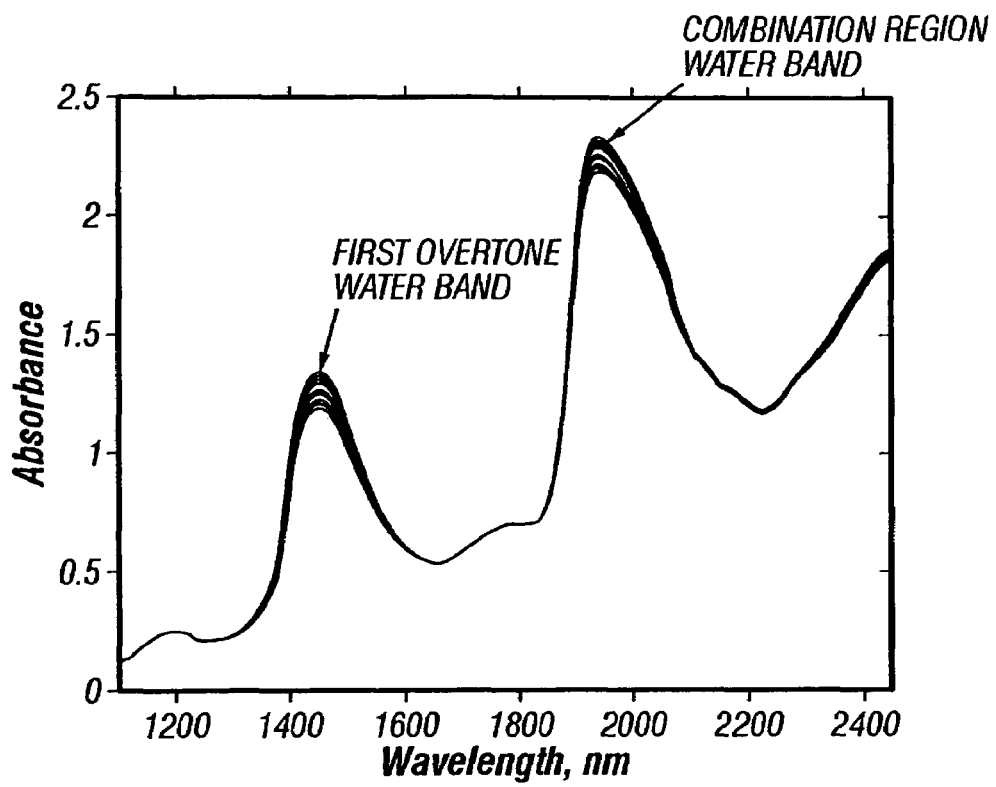
Figure 7B:
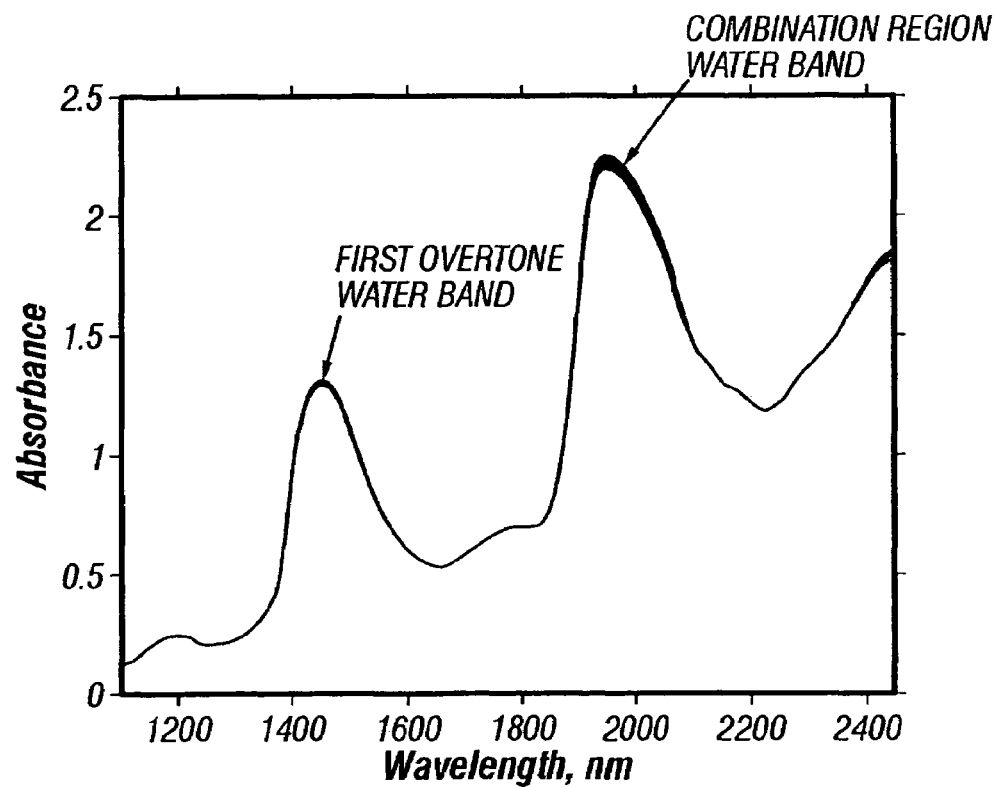

As a further illustration of the benefit of the guide placement system, sixty measurements were performed on a single subject with and without the guide positioning system. All spectra were collected using a custom built scanning near-infrared spectrometer. The instrument collected intensity spectra in diffuse reflectance from the forearm in the wavelength range 1050–2450 nm. The spectral sampling interval was 1 nm and the signal-to-noise ratio at the peak intensity was approximately 90 dB. The detectors used in the study were a combination of Indium-Gallium-Arsenide (InGaAs) and extended InGaAs detectors. The optical configuration consisted of a simple fiber-optic interface to the skin with a small (<2 mm) distance between the illumination and detection fibers. Reference spectra were recorded prior to each sample measurement by scanning a 99% SPECTRALON reflectance material and absorbance was calculated according to Equation (2). A cradle was developed to position the arm over the sample interface in a reproducible location with a reproducible degree of pressure, with the subject remaining seated during the experiment. In the first set of measurements, 60 samples were collected, each representing a different arm placement; and absorbance was calculated. In the second set of measurements, 60 samples were collected with the use of the guide positioning system. The absorbance spectra, shown plotted in FIG. 2, illustrate the benefit of using the guide positioning system. The plot of FIG. 6A shows the absorbance spectra over the 60 arm placements without the use of the guide positioning system. When the guide was used, the amount of spectral variation is significantly reduced (FIG. 6B).

Example 3

As a test of the benefit of the method of occlusion, 60 measurements were performed on a single subject using the apparatus described in Example 2. In the first set of measurements, 60 samples were collected using the guide positioning system without occlusion and absorbance was calculated as previously described. In the second set of measurements, 60 samples were collected with the use of both the guide positioning system and the preferred method of occlusion (a plug in the guide aperture). FIG. 6 shows the absorbance spectra collected without occlusion (FIG. 6A) and the absorbance spectra collected after occlusion (FIG. 6B). The decrease in surface variation associated with the water bands demonstrated the improved optical sampling realized as a result of the method of occlusion.

While the invented optical probe placement guide allows highly repeatable probe placement at a targeted tissue measurement site, the invention may also be used to produce small sampling variations in a controlled manner by shifting the placement of the optical probe in known increments across successive optical samples.

The invention provides a means of limiting sampling errors during in vivo spectroscopic examination of tissue samples by providing highly repeatable optical probe placement at a targeted tissue measurement site. Structural features of the invention minimize temperature fluctuations and variable stratum corneum hydration at the tissue measurement site and on the optical probe, and variations in tissue distortion and displacement, all sources of sampling error. An optional temperature probe in direct contact with the skin surface at the tissue measurement site allows the monitoring of skin temperature across successive measurements. An optical coupling fluid eliminates air spaces at the interface of the skin surface of the tissue measurement site and the optical probe. A fully hydrated stratum corneum is attained by the use of an occlusive plug or other mechanism. Finally, spectral measurements, and resulting analyte measurements are bias corrected to compensate error resulting from guide placement.

While the invented optical sampling interface system has been herein described in relation to optical sampling of tissue, one skilled in the art will appreciate that the invention may be applied in other settings requiring repeatable placement of an optical probe.

It is understood that each of the elements of the optical probe placement guide measurement system herein described are individually beneficial to the measurement and therefore can be used with or without the other elements. Specifically, the guide, the hydration control system, the coupling fluid, and the bias correction are uniquely beneficial. For example, in the event that an alternate mechanical positioning system is developed, the hydration control process, bias correction, and the coupling fluid are still beneficial.

Although the invention is described herein with reference to certain preferred embodiments, one skilled in the art will readily appreciate that other applications may be substituted for those set forth herein without departing from the spirit and scope of the present invention. Accordingly, the invention should only be limited by the claims included below.

The invention claimed is:

1. An optical sampling interface system comprising:
    an optical probe placement guide for controlling variations in sample volume;
    means for controlling surface reflection of an optical signal;
    an occlusion plug for stabilizing surface hydration of a measurement site, said occlusion plug adapted to fit into an aperture in said placement guide between measurements, wherein said occlusion plug is removably attached at an exterior surface of said guide;
    wherein sampling error is minimized, eliminated, reduced or compensated.

2. The system of claim 1, wherein said placement guide comprises:
    a mount having a contact surface, at least a portion of said contact surface being in contact with a surface proximate said measurement site during use; and
    an aperture, defined by said mount; adapted to receive said optical probe, wherein an area defined by said aperture comprises said measurement site;
    wherein said guide is removably attached at said measurement site so that said guide can repeatably couple said optical probe to the measurement site.

3. The system of claim 2, wherein means for attaching said guide comprises any of:
    an adhesive;
    at least one strap;
    at least one armband; and
    at least one suction element.

4. The system of claim 2, wherein size and shape of said aperture are matched to those of said optical probe, said probe fitting snugly Into said aperture, so that a mechanical registration in an x-y plane of said probe relative to said measurement site is provided, said guide further comprising at least one mechanical stop, said stop preventing overpenetration of said probe toward said measurement site, and providing registration along a z-axis of said probe relative to said measurement site.

5. The system of claim 2, said guide further comprising optical registration means wherein said probe is registered relative to said measurement site along any of x-, y-, and z-axes.

6. The system of claim 1, said means for controlling surface reflection comprising an optical coupling medium.

7. The system of claim 6, wherein said optical coupling medium comprises an optical coupling fluid.

8. The system of claim 7, wherein said optical coupling fluid comprises:
    one or more perfluoro compounds, wherein a quantity of said optical coupling fluid is placed at an interface of an optical probe and a measurement site, so that said probe and said measurement site are tightly optically coupled.

9. The system of claim 1, wherein shape and dimensions of a portion of said occlusion plug adapted to be received by said aperture mimics shape and dimensions of said aperture.

10. The system of claim 1, further comprising means for stabilizing surface temperature.

11. The system of claim 1, wherein said measurement site comprises a tissue measurement site and wherein surface tissue at said measurement site comprises skin, skin surface comprising stratum corneum.

12. The system of claim 11, further comprising means for correcting measurement bias resulting from one or both of variations in sampled volume and measurement conditions.

13. The system of claim 12, wherein said means for correcting measurement bias comprises:
    a noninvasive measurement system;
    a tissue template; and
    a calibration model;
    wherein measurement bias is compensated by:
        determining difference between a tissue measurement and a tissue template;
        mapping resulting difference to a measurement of a target analyte according to a calibration model; and
        applying a baseline adjustment to said analyte measurement.

14. The system of claim 13, wherein variations in sampled volume result from differences in placement of either an optical probe, or an optical probe placement guide between measurements.

15. The system of claim 13, wherein said tissue template is determined through one or more tissue measurements combined according to a predetermined data selection criterion during a measurement period.

16. The system of claim 13, wherein said calibration model is determined from a calibration set of exemplary paired data points each consisting of a pre-processed and bias corrected tissue measurement and an associated reference analyte value determined from an analysis of a blood or interstitial fluid sample.

17. The system of claim 13, wherein said baseline adjustment is associated with said tissue template and said calibration model.

18. An apparatus for minimizing optical sampling error at a tissue measurement site due to fluctuations of surface conditions, comprising:
    an element defining a probe aperture, wherein said element is fabricated from a flexible material, wherein said element provides for stabilization of the measurement site and deformation of underlying tissue without applying undue force to a targeted tissue volume;
    an occlusion plug for insertion into said aperture between measurements; and
    means for removably attaching said plug at an exterior surface of said element defining said probe aperture.

19. The apparatus of claim 18, wherein shape and dimensions of at least a portion of said occlusion plug mimic shape and dimensions of said aperture.

20. The apparatus of claim 18, wherein said plug fits snugly within said aperture without additional attachment means.

21. The apparatus of claim 18, wherein said means for attaching comprises any of:

magnets attached to said plug and said apparatus bearing said probe aperture;
hook and loop tape;
adhesives; and
snaps.

22. The apparatus of claim 18, wherein said element bearing said probe aperture induces a tissue meniscus within said aperture.

23. The apparatus of claim 22, wherein said plug is adapted to stabilize hydration level of surface tissue across surface of said meniscus.

24. The apparatus of claim 18, wherein said element defining said aperture comprises an optical probe placement guide.

* * * * *